United States Patent [19]

Merritt et al.

[11] Patent Number: 5,003,065

[45] Date of Patent: Mar. 26, 1991

[54] COMPOUNDS AND PROCESS FOR MEASURING C-REACTIVE PROTEIN

[76] Inventors: Carey Merritt, 2617 E. Main St., Cato, N.Y. 13033; James Winkelman, 62 Rangeley Rd., Brookline; Ruth Silberman-Hazony, 11 Scotney Rd., Newton, both of Mass. 02167

[21] Appl. No.: 206,592

[22] Filed: Jun. 14, 1988

[51] Int. Cl.$^5$ ............... C07D 498/16; C07F 9/06; G01N 33/00

[52] U.S. Cl. .................... 540/469; 540/452; 549/208; 549/220; 549/349; 549/351; 436/86

[58] Field of Search ............... 540/469, 452; 549/349, 549/351, 220, 208

[56] References Cited

U.S. PATENT DOCUMENTS

| | | | |
|---|---|---|---|
| 3,888,877 | 6/1975 | Lehn | 260/327 |
| 4,739,081 | 4/1988 | Toke et al. | 549/351 |
| 4,876,367 | 10/1989 | Urban | 549/349 |

FOREIGN PATENT DOCUMENTS

83/00149  1/1983  World Int. Prop. O. ........ 549/351

OTHER PUBLICATIONS

Gabetta et al., Chem. Abst. 101-121086u (1987).
Merritt et al., Chem. Abst. 111-190570s (1989).
Comparative Studies on the Binding Properties of Human and Rabbit C-Reactive Proteins; Eduardo B. Oliveira et al.; The Journal of Immunology; vol. 124, No. 3, Mar. 1980.
Synthesis of Two Novel Phosphorylcholine Esters For Probes in Immunological Studies; Thomas F. Spande; Published 1980 by the American Chemical Society.
Affinity Labeling of a Phosphorylcholine Binding Mouse Myeloma Protein; Biochemistry, vol. 11, No. 5, 1972, Bruce Chesebro et al.
Synthesis and Use of New Spin Labeled Derivatives of Phosphorylcholine in a Comparative Study of Human, Dogfish, and Limulus C-Reactive Proteins; Robey et al. The Journal of Biological Chemistry, vol. 258, No. 6, Mar. 1983, pp. 3895-3900.
Biology of C-Reactive Protein and the Acute Phase Response; Henry Gewurz; Hospital Practice, Jun. 1982, pp. 67-81.
Crown Compounds; Michio Hiraska; Elsevier Scientific Publishing Co. 1982.
Antibody Binding Measurements With Hapten-Selective Membrane Electrodes; M. Meyerhoff et al., Science, vol. 195, Feb. 1977, pp. 494-495.
Antibody-Selective Membrane Electrodes; R. L. Solsky et al., Science, vol. 204, Jun. 1979, pp. 1308-1309.
Cortisol Antibody Electrode; M. Y. Keating et al., Analyst, Jun. 1983, pp. 766-768.
Preparation and Properties of an Antibody Selective Membrane Electrode; R. L. Solsky et al., Analytica Chimica Acta, 123 (1981) 135-141.
Potentiometric Digoxin Antibody Measurements With Antigen-Ionophore Based Membrane Electrodes; M. Y. Keating et al., Anal. Chem. 1984, 56, pp. 801-806.
Antigen-Antibody Reaction Investigated With Use of a Chemically Modified Electrode; Naoto Yamamoto et al., Clinical Chemistry, vol. 26, No. 11, 1980, pp. 1569-1572.
The Affinity Electrode; C. R. Lowe, Febs Letters, vol. 106, No. 2, Oct. 1979, pp. 405-408.
Enzyme-Linked Immunoassay of Human Immunoglobulin G With The Fluoride Ion Selective Electrode; Peter W. Alexander et al., Analytical Chemistry, vol. 54, No. 1, Jan. 1982, pp. 68-71.
Immobilization of Anti HR$_2$Ag Antibodies on Artificial Proteic Membranes; Boitieux et al., Febs Letters, vol. 93, No. 1, Sep. 1978, pp. 133-136.
The Electrical Method of Investigation of the Antigen-Antibody and Enzyme-Enzyme Inhibitor Reactons Using Chemically Modified Electrodes; Chemistry Letters, pp. 245-246, 1978, Published by Chemical Society of Japan. Yamamoto et al.
Liposome Immunoelectrode; Chemistry Letters, pp. 155-158, 1980, Shiba et al. Published by Chemical Society of Japan.
Cyclic Polyethers and Their Complexes With Metal Salts; C. J. Pedersen, Journal of the American Chemical Society, Dec. 1967; pp. 7017-7036.
Potassium-Selective Electrodes Based on Macrocyclic Polyethers; J. Petranek et al., Analytica Chimica Acta. 72 (1974) pp. 375-380.

(Abstract on page 2)

5,003,065

*Primary Examiner*—Cecilia Shen
*Attorney, Agent, or Firm*—Michael L. Dunn; William J. Crossetta; Anna E. Mack

[57] ABSTRACT

New compounds are described of the formula:

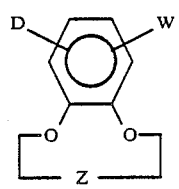

wherein Z is selected from

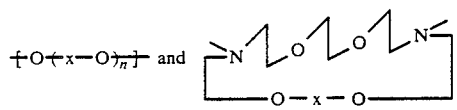

each x is selected from

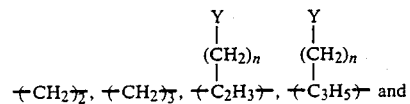

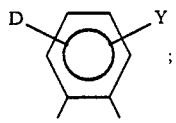

n is an integer from 1–10; each Y is selected from hydrogen, $-NH_2$, $-COQ$, $-COOQ$, $-COONHQ$, $-COOH$, $-OH$, W, halogen and Q; wherein each Q is independently selected from substituted and unsubstituted lower alkenyl and lower alkyl and wherein the substitutuents are selected from $-NH_2$, halogen, $-OH$, and $-COOH$; D is selected from hydroxy, hydrogen and $-NH_2$; and W is selected from

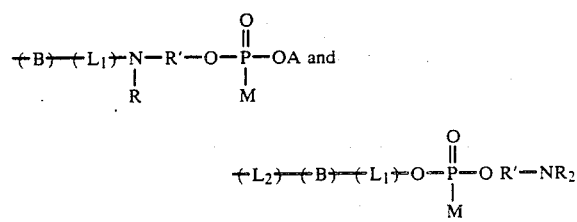

wherein each R is independently selected from hydrogen and lower alkyl; R' is selected from ethylene, propylene, isopropylene and phenylene; M is selected from chlorine and hydroxy; A is selected from hydrogen, lower alkyl, lower alkenyl, cycloalkyl, and phenyl; (B) is selected from

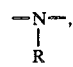

$-CO-$, $-NHCO-$, $-O-$, $-COO-$, $-N=N-$, or represents a confugate bond; $L_1$ and $L_2$ are selected from hydroxy substituted or unsubstituted lower alkyl, cycloalkyl, lower alkenyl, or phenyl; providing $L_2$ can be a conjugate bond. These compounds have specific utility in a process, for measuring c-reactive protein by binding with c-reactive protein and acting to release metal ions and/or inhibit the flow of the metal ion complex under electrochemically measurable conditions.

42 Claims, 1 Drawing Sheet

FIG. 1

FIG. 2

COMPOUNDS AND PROCESS FOR MEASURING C-REACTIVE PROTEIN

This invention relates to novel compounds and a process for their use in a method for the quantitative measurement of c-reactive protein in the determination of the extent of trauma suffered by a warm blooded animal.

BACKGROUND OF THE INVENTION

In the last several decades, the medical community has expressed increasing dissatisfaction with existing methods of determining the level of trauma being experienced by human and other warm blooded animals during trauma provoking incidents. Practitioners of the medical arts are particularly desirous of having available as a quick, simple, and accurate diagnostic tool, a means for ascertaining the trauma level of a patient under stress so that a proper medicament, in appropriate amounts, can be prescribed.

It has long been known that stimuli to warm blooded animals, such as cellular injury, inflammation, and even pregnancy can cause the animal body to produce various proteins, commonly called the acute phase proteins. One particular type of acute phase protein, known as the c-reactive protein (CRP), has been found to be particularly susceptible to dramatic increases upon the imposition of stimuli to the animal body and much data has been accumulated concerning the presence of this protein in the circulatory system under various conditions of trauma. CRP is thought to be functionally integral with the effecters of the immunologic and inflammatory response systems and during the last several decades its presence has been used to help diagnose the presence and extent of inflammation as well as tissue necrosis.

Experimental research has shown that CRP levels in the animal body intimately follows the course of the acute phase in trauma and monitoring CRP has been used with success to provide a valuable clinical barometer of illness. Thus CRP measurement is considered by many diagnosticians as a refined quantitative alternate and/or supplement to erythrocyte sedimentation rate in diagnostic medicine. Confirmation of the benefits and utility of quantitative measurement of c-reactive protein can be found in: *Biology of C-Reactive Protein and the Acute Phase Response*, Hospital Practice, June 1982, Dr. Henry Gewurz; *C. Reactive Protein and the Plasma Protein Response to Tissue Injury*, A. Symposium, VOL. 389, N.Y. Academy of Science, N.Y., 1982, Kushner I. Volanakis et al.; *C-Reactive Protein is Protection Against S. pneumoniae Infection in Mice.* J. Exp. Med. 154:1703, 1981, C. Mold et al.; and *Primary Structure of Human C-Reactive Protein*, J. Biol. Chem. 254:489, 1979, E.B. Oliveira et al.

Thus, one object of this invention is to provide a convenient method for monitoring the extent of trauma experienced by an animal body. Another object of the invention is to provide a method to monitor an acute phase protein. Still another object of the invention is to provide new compounds which are useful for monitoring CRP. A further object is to provide new compounds capable of complexing with metal ions. A still further objective is to provide new compounds from which, in a polymer membrane the presence of CRP can be measured by electrochemical change. These and other objects of the invention will become apparent from the following recitation.

SUMMARY OF THE INVENTION

We have found that when a protonated c-reactive protein specific binding compound is complexed with a metal ion and is comprised in a membrane, that upon binding of CRP, the electrochemical potential across the membrane undergoes a change which can be electrochemically measured. This electrochemical potential variation appears to be a direct function of the quantity of CRP bound by the binding compound. This relationship between the electrochemical measurement and the binding of CRP provides the basis for the process of the invention and its utility to ascertain CRP levels in human blood samples.

In accordance with the method of this invention, new phosphate containing cyclic polyether compounds are disclosed of the formula:

wherein Z is selected from each x is selected from n is an integer from 1–10; each Y is selected from hydrogen, —NH$_2$, —COOQ, —COQ, —CONHQ, —COOH, —OH, W, halogen and Q; wherein Q is independently selected from substituted and unsubstituted lower alkenyl and lower alkyl and wherein the substituents are selected from —NH$_2$, halogen, —OH, and —COOH; D is selected from hydroxy, hydrogen and —NH$_2$; and W is selected from wherein each R is independently selected from hydrogen and lower alkyl; R' is selected from ethylene, propylene, isopropylene and phenylene; M is selected from chlorine and hydroxy; A is selected from hydrogen, lower alkyl, lower alkenyl, cycloalkyl, and phenyl; (B) is selected from —CO—, —NHCO—, —O—, —COO—, —N=N—, or represents a conjugate bond; and ­-$L_1$-­ and ­-$L_2$-­ are selected from hydroxy substituted or unsubstituted lower alkylene, cycloalkylene, lower alkenylene, or phenylene; providing ­-$L_2$-­ can be a conjugate bond.

The new phosphate containing cyclic polyether compounds of the invention are particularly effective at forming complexes with the salts of the metals, particularly lithium, potassium, sodium, cesium, rubidium, calcium and magnesium, belonging to Groups I and II of the periodic table.

Accordingly, new CRP binding metal complexes are also disclosed of the formula:

wherein E is a metal ion selected from Groups I and II of the periodic table, D, W and Z are as previously described and m is an integer from 1–10.

The metal complexes appear to be salt-polyether complexes formed by ion-dipole interaction between the cation and the negatively charged oxygen atoms symmetrically placed in the cyclic polyether ring.

Generally, it was found that the stability of the cyclic polyether-metal ion complex depends on the size similarity of the metal ion atomic radius and the internal oxygen rich cavity. The polyether ring portion of the complex compound is generally known as a crown or krytofix ether structure, the chemical terminology thereof being well known in the prior art. The formation of the complex between the phosphate containing cyclic polyether and the metal salts depends in part upon the changes in solubility of the polyether and metal salts in different solvents. Generally, we have found the better solvents to be methanol, ethanol and other moderately unpolar solvents such as tetrahydrofuran and the like. Several methods of complexing cyclic polyether with metal salts, which are applicable to the present invention and are well known in the art, can be found at *Cyclic Polyethers and Their Complexes With Metal Salts*, J. Am. Chem. Soc. 89:7017 (1967) C. J. Pedersen. Typically, the preferred metal ions to complex with the polyethers of the invention are potassium and sodium.

Within the description of the phosphate containing cyclic polyether compounds of this invention, the terms lower alkyl and lower alkenyl are meant to include alkyl and alkenyl substituents having from 1 to about 10 carbon atoms and preferably from 1 to about 7 carbon atoms. Such substituents can be either straight chained or branched and include isomers thereof. Thus the term lower alkyl includes methyl, ethyl, n-propyl, i-propyl, m-butyl, s-butyl, pentyl, hexyl and the like up to about 10 carbon atoms; while the term lower alkenyl includes unsaturated hydrocarbons having one or more double bonds therein and includes ethene, propene, butene, pentene, and the like up to about 10 carbon atoms. Similarly, by the terms lower alkylene and lower alkenylene is meant lower alkyl and lower alkenyl as abovedescribed additionally designated, however, as comprising available bonding sites for attachment within the base structure of the compounds of the invention.

By the term cycloalkyl is meant a univalent radical formed by the removal of one or two hydrogen atoms from a cycloalkane and is meant to include cycloalkyl substituents of up to about 10 carbon atoms such as cyclopentyl, cyclohexyl and the like. Similarly, cycloalkylene refers to cycloalkyl additionally containing available bonding sites for attachment within the base structure.

Typical phosphate containing cyclic polyether compounds falling within the disclosure of this invention include:

4, benzo 15 crown 5(6-0-phosphorylcholine)hydroxyhexamide;

N, benzo 15 crown 5(1-0-phosphorylcholine)hydrodroxyacetamide;

(benzo 15 crown 5)4 propanol(-0-phosphorylcholine);

(benzo 15 crown 5)4-aminohydroxymethyl(-0-phosphorylcholine);

4-hydroxy(benzo 15 crown 5)3-paradiazophenylphosphorylcholine;

benzo 15 crown 5, 4(-ethoxy-0-phosphorylcholine);

0-phosphorylcholine methyl 4-benzoate 15 crown 6;

benzo 15 crown 5, 4(-0-phosphosphorylcholine methylate);

benzo 15 crown 5, 4(-0-phosphorylcholine ethanoate);

N, hydroxymethyl 0-phosphorylcholine benzamide 15 crown 5;

4-hydroxy benzo 15 crown 5,3 paradiazophenyl 1-hydroxymethyl 0-phosphorylcholine;

(4-methyl benzo 15 crown 5)-0-phosphorylcholine hydroxy 6-hexanoate;

(4-methyl benzo 15 crown 5)-0-phosphorylcholine hydroxy 5-pentamide;

(4-methyl benzo 15 crown 5)-0-phosphorylcholine hydroxy 5-heptal ether;

(4-methyl benzo 15 crown 5)-0-phosphorylcholine hydroxyhexamine;

(4-amino benzo 15 crown 5)3-paradiazophenyl 1-hydroxyhexyl 0-phosphorylcholine;

4(phosphoethanolamine)methyl benzo 15 crown 5;

4-amido(methylphosphoethanolamine)benzo 15 crown 5;

4-ethyl(p-aminophenylphosphate)benzo 15 crown 5;

4-(aminophenylphosphorylcholine)methyl benzo 15 crown 5;

4-(p-aminophenylphosphate-0-)methyl benzo 15 crown 5;

4-amido benzo 15 crown 5(6-phenylhexyl-0-phosphorylcholine);

4, krytofix 222B(6-0-phosphorylcholine)hydroxyhexamide;

N, krytofix 222B(1-0-phosphorylcholine)hydrodroxyacetamide;

(krytofix 222B)4 propanol(-0-phosphorylcholine);

(krytofix 222B)4-aminohydroxymethyl(-0-phosphorylcholine);
4-hydroxy(krytofix 222B)3-paradiazophenylphosphorylcholine;
krytofix 222B, 4(-ethoxy-0-phosphorylcholine);
0-phosphorylcholine methyl 4-krytofix 222B;
krytofix 222B, 4(-0-phosphorylcholine methylate);
krytofix 222B, 4(-0-phosphorylcholine ethanoate);
N, hydroxymethyl 0-phosphorylcholine krytofix 222B;
4-hydroxy krytofix 222B,3 paradiazophenyl 1-hydroxymethyl 0-phosphorylcholine;
(4-methyl krytofix 222B)-0-phosphorylcholine hydroxy 6-hexanoate;
(4-methyl krytofix 222B)-0-phosphorylcholine hydroxy 5-pentamide;
(4-methyl krytofix 222B)-0-phosphorylcholine hydroxy 5-heptal ether;
(4-methyl krytofix 222B)-0-phosphorylcholine hydroxyhexamine;
(4-amino krytofix 222B)3-paradiazophenyl 1-hydroxyhexyl 0-phosphorylcholine;
4(phosphoethanolamine)methyl krytofix 222B;
4-amido(methylphosphoethanolamine)krytofix 222B;
4-ethyl(p-aminophenylphosphate)krytofix 222B;
4-(aminophenylphosphorylcholine)methyl krytofix 222B;
4-(p-aminophenylphosphate-0-)methyl krytofix 222B;
4-amido krytofix 222B(6-phenylhexyl-0-phosphorylcholine);
4, amino dibenzo 18 crown 6,4'-(6-0-phosphorylcholine)hydroxyhexamide;
N, dibenzo 18 Crown 6(1-0-phosphorylcholine)hydrodroxyacetamide;
(dibenzo 18 crown 6)4 propanol(-0-phosphorylcholine);
(dibenzo 18 crown 6)4-aminohydroxymethyl(-0-phosphorylcholine);
4-hydroxy(dibenzo 18 crown 6)3-paradiazophenylphosphorylcholine;
dibenzo 18 crown 6, 4(-ethoxy-0-phosphorylcholine);
0-phosphorylcholine methyl 4-dibenzo 18 crown 6;
dibenzo 18 crown 6, 4(-0-phosphorylcholine methylate);
dibenzo 18 crown 6, 4(-0-phosphorylcholine: ethanoate);
N, hydroxymethyl 0-phosphorylcholine dibenzo 18 crown 6;
4-hydroxy dibenzo 18 crown 6,3 paradiazophenyl 1-hydroxymethyl 0-phosphorylcholine;
(4-methyl dibenzo 18 crown 6)-0-phosphorylcholine hydroxy 6-hexanoate;
(4-methyl dibenzo 18 crown 6)-0-phosphorylcholine hydroxy 5-pentamide;
(4-methyl dibenzo 18 crown 6)-0-phosphorylcholine hydroxy 5-heptal ether;
(4-methyl dibenzo 18 crown 6)-0-phosphorylcholine hydroxyhexamine;
(4-amino dibenzo 18 crown 6)3-paradiazophenyl 1-hydroxyhexyl 0-phosphorylcholine;
4( When an hydroxy substituent is desired, an appropriate substituted sulfonyl moiety is carried through from the reactants. The sulfonyl moiety is thereafter treated with NaOH in the presence of heat and the resulting product protonated with HCl at acid pH to form the hydroxy substituent. When an acid moiety is desired, an appropriate alkyl acetyl group is carried through from the reactants and thereafter oxidized with bromine and NaOH to form the acid. Thus, the manner and method of attaining the appropriate T substituents is generally not complex and easily accomplished.

The phosphorus containing esters, appropriate for reaction with the cyclic polyethers above-described are of the base structure:

wherein R is independently selected from hydrogen and lower alkyl; R' is selected from ethylene, propylene, isopropylene and phenylene; M is selected from chlorine and hydroxy; A' is selected from hydrogen, lower alkyl, lower alkenyl, cycloalkyl, phenyl, substituted lower alkyl, cycloalkyl, lower alkenyl and phenyl wherein the substituents are selected from COOH, OH, NH$_2$, Cl, Br, I and nitrophenyl carboxylate.

In the phosphorus ester base structure, the A' or R moiety represents the bridging moiety of attachment comprising an active substituent for reaction with the active substituent of the benzo moiety of the polyether. The defined $-B-$, $-L_1-$ and $-L_2-$ substituents are formed as a product of the reaction.

The phosphorus ester base structures are well known in the prior art and are generally commercially available. Phosphate esters are generally prepared by adding phosphorus oxychloride slowly to an appropriate alcohol or phenyl containing compound to form the corresponding ester. The formation of the mixed esters of the invention wherein R' and A are the same or different and M is hydroxy or chlorine is prepared by adding the appropriate alcohol or phenyl to the phosphorus oxychloride so that the equivalent of alcohol will form a dichlorophosphate, the chlorine atom of which can be replaced by reaction with other alcohols.

The novel compounds of the invention have good ion complexing properties and readily react, in polar and moderately nonpolar solvents, with the salts of metals, particularly those of Groups I and II of the periodic table to form the metal complexes of the invention. The metal complexes of the invention in turn have a high affinity for CRP, such that when CRP is introduced to a solution of a metal complex of the invention, there is an immediate measurable disruption of voltage equilibrium of the metal complex. Incorporation of the metal complex compounds of the invention into a polymer membrane and affixing the membrane to the tip of an electrode assembly, or having an electrode comprising the membrane, provides a means for continual monitoring of voltage equilibrium of the membrane. Contact of such assembly with a CRP containing solution provides a measurable voltage disruption which can be used to determine the concentration of the CRP, thus providing a quick and efficient means of ascertaining extent of trauma.

The following examples are provided to further demonstrate the invention and are not meant to be limitations thereof.

EXAMPLE I

Preparation of 4-Bromo Methyl Benzo 15 Crown 5

4-methyl benzo 15 crown 5 was prepared from 4-methyl catechol and tetraethylene glycol dichloride in accordance with the procedure described in J. Am. Chem. Soc. 89:7017 (1967) by C. J. Pederson 200 mg (0.7 mM) of the methyl benzo 15 crown 5 was dissolved in 40 ml of dried carbon tetrachloride and stirred for 5 minutes under a nitrogen blanket. N-bromo succinimide (126 mg, 0.7 mM) was added and the mixture was stirred for an additional 5 minutes under the nitrogen blanket. The reaction mixture was placed in a 70° C. oil bath and irradiated with a 500 watt tungsten lamp for 30 minutes. The product was cooled in an ice bath, filtered and the solvent removed under reduced pressure. The resulting yellow oil was extracted with n-heptase at 60° C. resulting in the recovery of crystalline 4-bromomethyl benzo 15 crown 5, which was confirmed by NMR.

EXAMPLE II

Preparation of 4-(p-aminophenyl phosphocholine) methyl benzo 15 crown 5 p-Aminophenyl phosphocholine (75 mg, 0.27 mM) and sodium carbonate (50 mg) Were dissolved in 15 ml of 4:1 methanol/butanol. To the solution, 120 mg (0.33 mM) of 4-bromomethyl benzo 15 crown 5 in 4:1 butanol/methanol was added dropwise over 30 minutes with stirring. The solution was stirred for an additional 72 hours at 45° C. and methanol was thereafter removed at room temperature under reduced pressure. The solution was cooled to 10° C., filtered, and the butanol evaporated at 50° C. under reduced pressure. To the remaining :tar-like substance, 5 ml of chloroform was added, mixed and decanted off after centrifuging. The precipitate was washed with 5 ml of fresh CHCL$_3$ and isolated as before to yield 43 mg of the aboveidentified captioned product, confirmed by NMR.

EXAMPLE III

Preparation of 4-(p-aminophenyl phosphocholine) dimethyl dibenzo 18 crown 6

4,4' dimethyl dibenzo 8 crown 6 is prepared in accordance with the procedure described by J. Petranek and 0. Ryba, Analytical Chem. Acta. 72, 1974 at page 375 The 4,4' dimethyl dibenzo 18 crown 6 is thereafter brominated in accord with Example I by adding one equivalent of N-bromo succinimide to a mixture of the 18 crown 6 in dried carbon tetrachloride, stirring and irradiating with a tungsten lamp to form the 4-bromo methyl, 4'-methyl dibenzo 18 crown 6. Use of an excess of N-bromo succinimide produces the 4,4'-dibromomethyl dibenzo 18 crown 6.

The thus produced 4-bromomethyl, 4'-methyl dibenzo 18 crown 6 is thereafter conjugated with p-aminophenylphosphocholine by the method of Example II by reacting with 1.2 mMoles of the p-aminophenyl-phosphocholine and sodium carbonate dissolved in a 4:1 mixture of methanol/butanol. The 4,4'-(p-aminophenylphosphocholine) dimethyl dibenzo 18 crown 6 is similarly prepared utilizing 2.4 mMoles of the p- aminophenyl-phosphocholine with the 4,4'-dibromomethyl dibenzo 18 crown 6.

EXAMPLE IV

Preparation of 4, Benzo 15 Crown 5(6,o-phosphorylcholine) hydroxyhexamide p-Nitrophenyl 6-(o-phosphorylcholine) hydroxyhexanoate is synthesized in accordance with the procedure described by Thomas Sparde, *J. Org. Chem.* 45, 1980, page 3081. To this compound a 5 molar excess of 4-aminophenyl benzo 15 crown 5 is added in ethanol and stirred for one hour. A two fold molar excess of triethylamine is added and stirred for an additional 4 hours. The reaction mixture is then passed through an amberlite MB-1 resin (NH+, OH−form) and the captioned product is isolated in methanol effluent.

EXAMPLE V

Preparation of 4, Krytofix 222B (6-o-phosphorylcholine) hydroxyhexamide

Krytofix 222B is prepared in accordance with the procedure outlined in U.S. Pat. No. 3,888,877 to J.M. Lehn. The resulting product is nitrated in accordance with the procedure described by E. Shchor et al, *Journal of the American Chemical Society*, 95:12, June 13, 1973 to produce the 4 methyl benzo Krytofix 222B derivative and thereafter conjugated with p-Nitrophenyl 6-(o-phosphorylcholine) hydroxy hexamate to produce the captioned product in accord with the procedure described in Example IV and as generally described by F. Robey of The-Yung Liu, *The Journal of Biological Chemistry*, Vol. 258, No. 6, page 3895, 1983.

EXAMPLE VI

Preparation of 4-(phosphoethanolamine) methyl benzo 15 crown 5

4'-bromo methyl benzo 15 crown 5 is prepared in accordance with the procedure of Example 1. A solution of 1m M phosphoethanolamine in ethanol is prepared at a pH of 9.0 (NaOH) and about two mg of $NaHCO_3$ is added. 1.2mM of 4'-bromomethylbenzo 15 crown 5 in butanol is prepared and added dropwise to the phosphoethanolamine solution over a two hour period. The mixture is stirred for 24 hours at room temperature and the product is isolated by filtration and extraction to produce the captioned product.

EXAMPLE VII

Metal Complexes 4-(p-Aminophenyl phosphocholine) methyl benzo 15 crown 5 is dissolved in butanol to produce several samples of 10 mMolar concentration. Various salts are added to the samples and the complexing activity of the 4-(p-Aminophenyl phosphocholine) methyl benzo 15 crown 5 is observed with metal complexes forming as follows:

| Salt | Crown:Salt |
| --- | --- |
| AgNO | 1:1 |
| NaSCN | 1:1 |
| KS CN | 2:1 |
| $NH_4SCN$ | 2:1 |

EXAMPLE VIII

Electrochemical Measurements

Two membranes, containing different compounds of the invention, were produced by preparing a mixture containing 0.25 ml of dipental phthlate with 50 micrograms of 4-(p-aminophenyl phosphocholine)-methylbenzo 15 crown 5, or 5-(phosphoethanolamine)-methylbenzo 15 crown 5 and slowly adding the mixture to 200 mg of polyvinylchloride dissolved in 5 ml of tetrahydrofuran. The resulting products were poured into 48 mm glass petri dishes and allowed to slowly evaporate, overnight, to produce pliable transparent membranes. A 7 mm diameter round piece of each membrane was separately affixed to a Model 93 Orion ion selective electrode body using a standard configured electrode tip, modified by being manufactured from Delrin and containing a threaded flange for affixing the membrane to the end of the electrode. The electrode tip was filled with 0.01 m KCl and conditioned by soaking overnight in an aqueous buffer solution containing 0.01 M KCl, 0.01 $MCaCl_2$ and 0.01 M tris-hydroxymethyl aminomethane at pH 7.4.

Commercially obtained C-reactive protein (CRP) was exhaustively dialyzed and diluted with the above-identified buffer solution to CRP concentrations of 0, 10, 50 and 100 μg/ml. Equal [K+] between all CRP dilutions and the reference buffer solution was confirmed by using a K+ion selective electrode.

The membrane tipped electrodes were used in conjunction with a standard ceramic frit reference electrode connected to a pH/MV meter. Electrochemical measurements were obtained by measuring the voltage of the reference buffer solution then one of the CRP buffer solutions. All solutions were gently stirred during measurement. The electrodes were blotted dry after voltage measurement from the reference buffer solution and were rinsed with 50 mm EDTA and then distilled water after voltage measurements were obtained from CRP buffer solutions.

Figure 1:
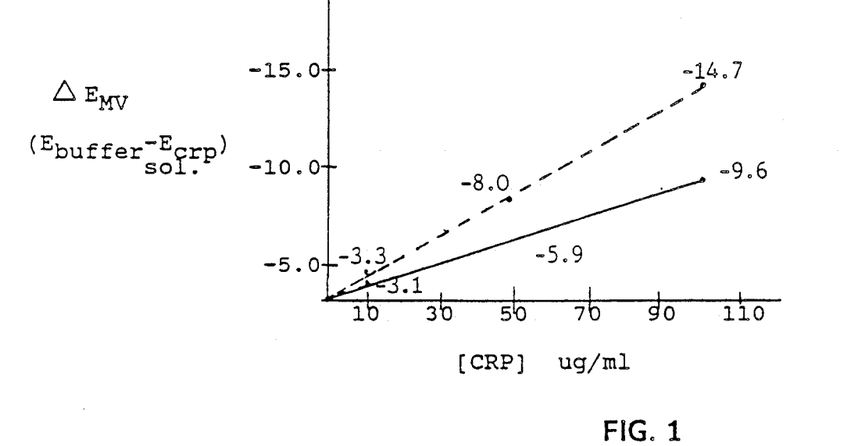

FIG. 1 comprises a plot of the difference in voltage measured between the buffer solution and the CRP buffer solution for the various CRP concentrations above-identified. The solid plot represents the results obtained using the membrane formed from the compound of Example II, the dotted plot, that of Example VI. As is readily apparent the voltage change is directly related to the CRP concentration for both membranes.

Figure 2:
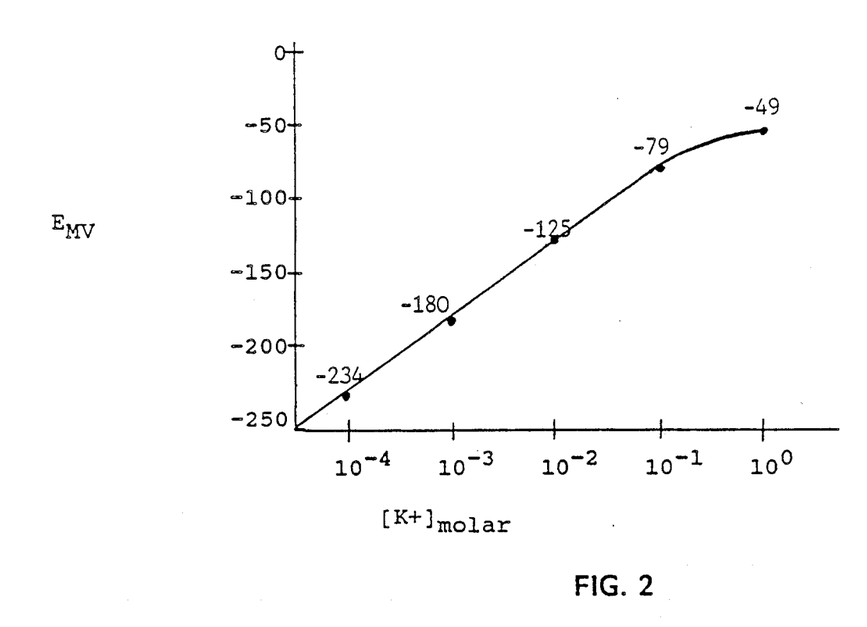

Additional buffer solutions were prepared containing KCl concentrations ranging from $1 \times 10^\circ - 10^{-4}$ molar. The membrane tipped electrode was used to obtain voltage measurements of the solution. FIG. 2 comprises a plot of the voltage measurements of the buffer solutions. The electrode displayed near Nerstein behavior toward charges in [K+] concentrations, the difference being those typically experienced with biosensor electrodes as reported in N.Y. Keating and G.A. Rechnitz, *Potentiometric Digitoxin Antibody Measurements With Antigen-Ionophore Base Membrane Electrodes, Analytical Chemistry*, Vol. 56, No. 4, April 1984, pg. 801.

What is claimed is:

1. A compound of the formula:

wherein Z is selected from each x is selected from n is an integer from 1-10; each Y is selected from hydrogen, —NH$_2$, —COQ, —COOQ, —CONHQ —COOH, —OH, W, halogen and Q, wherein each Q is independently selected from substituted and unsubstituted lower alkenyl and lower alkyl and wherein the substituents are selected from —NH$_2$, halogen, —OH, and —COOH; D is selected from hydroxy, hydrogen and —NH$_2$; and W is selected from wherein each R is independently selected from hydrogen and lower alkyl; R' is selected from ethylene, propylene, isopropylene and phenylene; M is selected from chlorine and hydroxy; A is selected from hydrogen, lower alkyl, lower alkenyl, cycloalkyl, and phenyl; (B) is selected from —CO—, —NHCO—, —O—, —COO—, —N=N—, or represents a conjugate bond; —(L$_1$)— and —(L$_2$)— are selected from hydroxy substituted or unsubstituted lower alkyl, cycloalkyl, lower alkenyl, or phenyl; providing —(L$_2$)— can be a conjugate bond.

2. A compound of claim 1 wherein Z is —(O—(X—O)$_n$)—.

3. A compound of claim 1 wherein Z is

4. A compound of claim 1 wherein x is selected from (CH$_2$)$_2$ and (CH$_2$)$_3$.

5. A compound of claim 1 wherein at least one W is

6. A compound of claim 1 wherein at least one W is

7. A compound of claim 5 wherein D is hydrogen and x is selected from (CH$_2$)$_2$ and (CH$_2$)$_3$.

8. A compound of claim 6 wherein D is hydrogen and X is selected from —(CH$_2$)—$_2$ and —(CH$_2$)—$_3$.

9. A compound of claim 5 wherein at least one x is

10. A compound of claim 6 wherein at least one x is

11. A compound of claim 5 wherein at least one —(B)— is —(N=N)—.

12. A compound of claim 5 wherein at least one —(B)(L$_1$)— is selected from —CH$_2$— and —CO—.

13. A compound of claim 9 wherein Y is W.

14. A compound of claim 10 wherein Y is W.

15. A compound of claim 1 selected from 4, benzo 15 crown 5(6-0-phosphorylcholine)hydroxyhexamide; N, benzo 15 crown 5(1-0-phosphorylcholine)hydrodroxyacetamide; (benzo 15 crown 5)4 propanol(-0-phosphorylcholine); (benzo 15 crown 5)4-aminohydroxymethyl-(-0-phosphorylcholine); 4-hydroxy(benzo 15 crown 5)3-paradiazophenylphosphorylcholine; benzo 15 crown 5, 4(-ethoxy-0-phosphorylcholine); 0-phosphorylcholine methyl 4-benzoate 15 crown 6; benzo 15 crown 5, 4(-0-phosphorylcholine methylate); benzo 15 crown 5, 4(-0-phosphorylcholine ethanoate); N, hydroxymethyl 0-phosphorylcholine benzamide 15 crown 5; 4-hydroxy benzo 15 crown 5,3 paradiazophenyl 1-hydroxymethyl 0-phosphorylcholine; (4-methyl benzo 15 crown 5)-0-phosphorylcholine hydroxy 6-hexanoate; and (4-methyl benzo 15 crown 5)-0-phosphorylcholine hydroxy 5-pentamide.

16. A compound of claim 1 selected from (4-methyl benzo 15 crown 5)-0-phosphorylcholine hydroxy 5-heptal ether; (4-methyl benzo 15 crown 5)-0-phosphorylcholine hydroxyhexamine; (4-amino benzo 15 crown 5)3-paradiazophenyl 1-hydroxyhexyl 0-phosphorylcholine; 4(phosphoethanolamine)methyl benzo 15 crown 5; 4-amido(methylphosphoethanolamine)benzo 15 crown 5; 4-ethyl(p-aminophenylphosphate)benzo 15 crown 5; 4-(aminophenylphosphorylcholine) methyl benzo 15 crown 5; 4-(p-aminophenylphosphate-0-)methyl benzo 15 crown 5; and 4-amido benzo 15 crown 5(6-phenylhexyl-0-phosphorylcholine).

17. A compound of claim 1 selected from 4, krytofix 222B(6-0-phosphorylcholine)hydroxyhexamide; N, krytofix 222B(1-0-phosphorylcholine)hydrodroxyacetamide; (krytofix 222B)4 propanol (-0-phosphorylcholine); (krytofix 222B)4-aminohydroxymethyl(-0-phosphorylcholine); 4-hydroxy(krytofix 222B)3-paradiazophenylphosphorylcholine; krytofix 222B, 4(-ethoxy-0-phosphorylcholine); 0-phosphorylcholine methyl 4-krytofix 222B; krytofix 222B, 4(-0-phosphosphorylcholine methylate); krytofix 222B, 4(-0-phosphorylcholine ethanoate); N, hydroxymethyl 0-phosphorylcholine krytofix 222B; and 4-hydroxy krytofix 222B,3 paradiazophenyl 1-hydroxymethyl 0-phosphorylcholine.

18. A compound of claim 1 selected from (4 TM methyl krytofix 222B)-0-phosphorylcholine hydroxy 6-hexanoate; (4-methyl krytofix 222B)-0-phosphorylcholine hydroxy 5-pentamide; (4-methyl krytofix 222B)-0-phosphorylcholine hydroxy 5-heptal ether; (4-methyl krytofix 222B)-0-phosphorylcholine hydroxyhexamine., (4-amino krytofix 222B)3-paradiazophenyl 1-hydroxyhexyl 0-phosphorylcholine; 4(phosphoethanolamine)methyl krytofix 222B; 4-amido(methylphosphoethanolamine)krytofix 222B; 4-ethyl(p-aminophenylphosphate)krytofix 222B; 4-(aminophenylphosphorylcholine)methyl krytofix 222B; 4-(p-aminophenylphosphate-0-)methyl krytofix 222B; and 4-amido krytofix 222B(6-phenylhexyl-0-phosphorylcholine).

19. A compound of claim 1 selected from 4, dibenzo 18 crown 6(6-0-phosphorylcholine)hydroxyhexamide; N, dibenzo 18 crown 6(1-0-phosphorylcholine)hydrodroxyacetamide; (dibenzo 18 crown 6)4 propanol(-0-phosphorylcholine); (dibenzo 18 crown 6)4-aminohydroxymethyl(-0-phosphorylcholine); 4-hydroxy(-dibenzo 18 crown 6)3-paradiazophenylphosphorylcholine; dibenzo 18 crown 6, 4(-ethoxy-0-phosphorylcholine); 0-phosphorylcholine methyl 4-dibenzo 18 crown 6; dibenzo 18 crown 6, 4(-0-phosphosphorylcholine methylate); dibenzo 18 crown 6, 4(-0-phosphorylcholine ethanoate); N, hydroxymethyl 0-phosphorylcholine dibenzo 18 crown 6; and 4-hydroxy dibenzo 18 crown 6,3 paradiazophenyl 1-hydroxymethyl 0-phosphorylcholine.

20. A compound of claim 1 selected from (4-methyl dibenzo 18 crown 6)-0-phosphorylcholine hydroxy 6-hexanoate; (4-methyl dibenzo 18 crown 6)-0-phosphorylcholine hydroxy 5-pentamide; (4-methyl dibenzo 18 crown 6)-0-phosphorylcholine hydroxy 5-heptal ether; (4-methyl dibenzo 18 crown 6)-0-phosphorylcholine hydroxyhexamine; (4-amino dibenzo 18 crown 6)3-paradiazophenyl 1-hydroxyhexyl 0-phosphorylcholine; 4(phosphoethanolamine)methyl dibenzo 18 crown 6; 4-amido(methylphosphoethanolamine)dibenzo 18 crown 6; 4-ethyl(p-aminophenylphosphate)dibenzo 18 crown 6; 4-(aminophenylphosphorylcholine)methyl dibenzo 18 crown 6; 4-(p-aminophenylphosphate-0-)methyl dibenzo 18 crown 6; and 4-amido dibenzo 18 crown 6(6-phenylhexyl-0-phosphorylcholine).

21. A phosphorus containing polyether, metal complex, compound of the formula:

wherein Z is selected from each x is selected from n is an integer from 1–10; each Y is selected from hydrogen, —NH$_2$, —COQ, COOQ, CONHQ, —COOH, —OH, W, halogen and Q, wherein each Q is independently selected from substituted and unsubstituted lower alkenyl and lower alkyl and wherein the substituents are selected from —NH$_2$, halogen, —OH, and —COOH; D is selected from hydroxy, hydrogen and —NH$_2$; and W is selected from wherein each R is independently selected from hydrogen and lower alkyl; R' is selected from ethylene, propylene, isopropylene and phenylene; M is selected from chlorine and hydroxy; A is selected from hydrogen, lower alkyl, lower alkenyl, cycloalkyl, and phenyl; —B— is selected from —CO—, —NHCO—, —O—, —COO—, —N=N—, or represents a conjugate bond; and +L$_1$+ and +L$_2$+ are selected from hydroxy substituted or unsubstituted lower alkyl, cycloalkyl, lower alkenyl, or phenyl; providing $-L_2-$ can be a conjugate bond; E is a metal ion selected from Groups I and II of the periodic table and m is an integer from 1-10.

22. A compound of claim 21 wherein Z is $-O-$ $\times -O_n-$].

23. A compound of claim 21 wherein Z is

24. A compound of claim 21 wherein x is selected from $-CH_2-_2$ and $-CH_2-_3$.

25. A compound of claim 21 wherein at least one W is

26. A compound of claim 21 wherein at least one W is

27. A compound of claim 25 wherein D is hydrogen and x is selected from $-CH_2-_2$ and $-CH_2-_3$.

28. A compound of claim 26 wherein D is hydrogen and X is selected from $-CH_2-_2$ and $-CH_2-_3$.

29. A compound of claim 25 wherein at least one x is

30. A compound of claim 26 wherein at least one x is

31. A compound of claim 25 wherein at least one $-B-$ is $-N=N-$.

32. A compound of claim 25 wherein at least one $-B-(L_1-$ is selected from $-CH_2-$ and $-CO-$.

33. A compound of claim 29 wherein Y is W.

34. A compound of claim 30 wherein Y is W.

35. A compound of claim 21 wherein said metal ion is selected from lithium, potassium, sodium, cerium, rubidium, calcium and magnesium.

36. A compound of claim 35 wherein said metal ion is selected from sodium and potassium.

37. A compound of claim 35 wherein the phosphorus containing polyether is selected from 4, benzo 15 crown 5(6-0-phosphorylcholine)hydroxyhexamide; N, benzo 15 crown 5(1-0-phosphorylcholine)hydrodroxyacetamide; (benzo 15 crown 5)4 propanol(-0-phosphorylcholine); (benzo 15 crown 5)4-aminohydroxy-methyl(-0-phosphorylcholine); 4-hydroxy(benzo 15 crown 5)3-paradiazophenylphosphorylcholine; benzo 15 crown 5, 4(-ethoxy-0phosphorylcholine); 0-phosphorylcholine methyl 4-benzoate 15 crown 6; benzo 15 crown 5, 4(-0-phosphosphorylcholine methylate); benzo 15 crown 5, 4(-0-phosphosphorylcholine ethanoate); N, hydroxymethyl 0-phosphorylcholine benzamide 15 crown 5; 4-hydroxy benzo 15 crown 5,3 paradiazophenyl 1-hydroxymethyl Q-phosphorylcholine; (4-methyl benzo 15 crown 5)-0-phosphorylcholine hydroxy 6-hexanoate; and (4-methyl benzo 15 crown 5)-0-phosphorylcholine hydroxy 5-pentamide.

38. A compound of claim 35 wherein the phosphorus containing polyether is selected from (4-methyl benzo 15 crown 5)-0-phosphorylcholine hydroxy 5-heptal ether; (4-methyl benzo 15 crown 5)-0-phosphorylcholine hydroxyhexamine; (4-amino benzo 15 crown 5)3-paradiazophenyl 1-hydroxyhexyl 0-phosphorylcholine; 4(phosphoethanolamine)methyl benzo 15 crown 5; 4-amido(methylphosphoethanolamine)benzo 15 crown 5; 4-ethyl(p-aminophenylphosphate)benzo 15 crown 5: 4-(aminophenylphosphorylcholine) methyl benzo 15 crown 5; 4-(p-aminophenylphosphate-0-)methyl benzo 15 crown 5; and 4-amido benzo 15 crown 5(6-phenylhexyl-0-phosphorylcholine).

39. A compound of claim 35 wherein the phosphorus containing polyether is selected from 4, krytofix 222B(6-0-phosphorylcholine)hydroxyhexamide; N, krytofix 222B(1-0-phosphorylcholine)hydrodroxyacetamide; (krytofix 222B)4 propanol (-0-phosphorylcholine); (krytofix 222B)4-aminohydroxymethyl(-0-phosphorylcholine); 4-hydroxy(krytofix 222B)3-paradiazophenylphosphorylcholine; krytofix 222B, 4(-ethoxy-0-phosphorylcholine); 0-phosphorylcholine methyl 4-krytofix 222B; krytofix 222B, 4(-0-phosphosphorylcholine methylate); krytofix 222B, 4(-0-phosphosphorylcholine ethanoate); N, hydroxymethyl 0-phosphorylcholine krytofix 222B; and 4-hydroxy krytofix 222B,3 paradiazophenyl 1-hydroxymethyl 0-phosphorylcholine.

40. A compound of claim 35 wherein the phosphorus containing polyether is selected from (4-methyl krytofix 222B)-0-phosphorylcholine hydroxy 6-hexanoate; (4-methyl krytofix 222B)-0-phosphorylcholine hydroxy 5-pentamide; (4-methyl krytofix 222B)-0-phosphorylcholine hydroxy 5-heptal ether; (4-methyl krytofix 222B)-0-phosphorylcholine hydroxyhexamine; (4-amino krytofix 222B)3-paradiazophenyl 1-hydroxyhexyl 0-phosphorylcholine; 4(phosphoethanolamine)methyl krytofix 222B; 4amido(methylphosphoethanolamine)krytofix 222B; 4-ethyl(p-aminophenylphosphate)krytofix 222B; 4-(aminophenylphosphorylcholine)methyl krytofix 222B; 4-(p-aminophenylphosphate-0-)methyl krytofix 222B; and 4-amido krytofix 222B(6-phenylhexyl-0-phosphorylcholine).

41. A compound of claim 35 wherein the phosphorus containing polyether is selected from 4, dibenzo 18 crown 6(6-0-phosphorylcholine)hydroxyhexamide; N, dibenzo 18 crown 6(1-0-phosphorylcholine)hydrodroxyacetamide; (dibenzo 18 crown 6)4 propanol(-0-phosphorylcholine); (dibenzo 18 crown 6)4-aminohydroxymethyl(-0-phosphorylcholine); 4-hydroxy(dibenzo 18 crown 6)3-paradiazophenylphosphorylcholine; dibenzo 18 crown 6, 4(-ethoxy-0-phosphorylcholine); 0-phosphorylcholine methyl 4-dibenzo 18 crown 6; dibenzo 18 crown 6, 4(-0 -phosphosphorylcholine methylate); dibenzo 18 crown 6, 4(-0-phosphosphorylcholine ethanoate); N, hydroxymethyl 0-phosphorylcholine dibenzo 18 crown 6; and 4-hydroxy dibenzo 18 crown 6,3 paradiazophenyl 1-hydroxymethyl 0-phosphorylcholine.

42. A compound of claim 35 wherein the phosphorus containing polyether is selected from (4-methyl dibenzo 18 crown 6)-0-phosphorylcholine hydroxy 6-hexanoate; (4-methyl dibenzo 18 crown 6)-0-phosphorylcholine hydroxy 5-pentamide; (4-methyl dibenzo 18 crown 6)-0-phosphorylcholine hydroxy 5-heptal ether; (4-methyl dibenzo 18 crown 6)-0-phosphorylcholine hydroxyhexamine; (4-amino dibenzo 18 crown 6(3-paradiazophenyl 1-hydroxyhexyl 0-phosphorylcholine; 4(phosphoethanolamine)methyl dibenzo 18 crown 6; 4-amido(methylphosphoethanolamine)dibenzo 18 crown 6; 4-ethyl(p-aminophenylphosphate)dibenzo 18 crown 6; 4-(aminophenylphosphorylcholine)methyl dibenzo 18 crown 6; 4-(p-aminophenylphosphate-0-)methyl dibenzo 18 crown 6; and 4-amido dibenzo 18 crown 6(6-phenylhexyl0-phosphorylcholine).

* * * * *

UNITED STATES PATENT AND TRADEMARK OFFICE
CERTIFICATE OF CORRECTION

PATENT NO. : 5,003,065

DATED : March 26, 1991

INVENTOR(S) : Merritt et al

It is certified that error appears in the above-identified patent and that said Letters Patent is hereby corrected as shown below:

In Claim 1, column 11, lines 20-25

"  " should be deleted and should be substituted.

UNITED STATES PATENT AND TRADEMARK OFFICE
CERTIFICATE OF CORRECTION

PATENT NO. : 5,003,065

DATED : March 26, 1991

INVENTOR(S) : Merritt et al

It is certified that error appears in the above-identified patent and that said Letters Patent is hereby corrected as shown below:

In Claim 18, column 13, line 30 "TM" should be deleted.

In Claim 21, column 14, line 18, $--[O(X-O)_n]$ and -- should be inserted.

Signed and Sealed this

Twenty-fifth Day of August, 1992

*Attest:*

DOUGLAS B. COMER

*Attesting Officer*     *Acting Commissioner of Patents and Trademarks*

UNITED STATES PATENT AND TRADEMARK OFFICE
CERTIFICATE OF CORRECTION

PATENT NO. : 5,003,065
DATED : March 26, 1991
INVENTOR(S) : Carey Merritt et al.

It is certified that error appears in the above-identified patent and that said Letters Patent is hereby corrected as shown below:

On the cover page please add:

[73] Assignee: State University of New York, Albany, N.Y.

Signed and Sealed this

Eighth Day of December, 1992

Attest:

DOUGLAS B. COMER

Attesting Officer

Acting Commissioner of Patents and Trademarks